US000001114H

United States Statutory Invention Registration [19]

[11] Reg. Number: H1114

[43] Published: Dec. 1, 1992

Schweitzer et al.

[54] FIBER-OPTIC OXYGEN SATURATION/HEMATOCRIT SENSOR

[75] Inventors: Jeffrey A. Schweitzer, St. Paul; George P. Seifert, Shoreview, both of Minn.

[73] Assignee: Medtronic, Inc., Minneapolis, Minn.

[21] Appl. No.: 516,604

[22] Filed: Apr. 30, 1990

[51] Int. Cl.[5] ..... A61B 5/00

[52] U.S. Cl. ..... 128/634; 128/633

[58] Field of Search ..... 356/39, 40, 41; 128/633, 634; 350/96.15

[56] References Cited

U.S. PATENT DOCUMENTS

| | | | |
|---|---|---|---|
| 3,647,299 | 3/1972 | Lavallee | 356/41 |
| 4,114,604 | 9/1978 | Shaw et al. | 128/2 L |
| 4,295,470 | 10/1981 | Shaw et al. | 128/634 |
| 4,416,285 | 11/1983 | Shaw et al. | 128/634 |
| 4,449,535 | 5/1984 | Renault | 128/634 |
| 4,509,522 | 4/1985 | Manuccia ete al. | 128/634 |
| 4,621,894 | 11/1986 | Gouali | 350/96.15 |
| 4,623,248 | 11/1986 | Sperinde | 356/41 |
| 4,624,570 | 11/1986 | Bertollini | 356/373 |
| 4,651,741 | 3/1987 | Passafaro | 128/633 |
| 4,726,642 | 2/1988 | Mori | 350/96.15 |
| 4,776,340 | 10/1988 | Moran et al. | 128/634 |

*Primary Examiner*—Bernarr E. Gregory

*Attorney, Agent, or Firm*—Reed A. Duthler; Harold R. Patton

[57] ABSTRACT

A two fiber reflectance oximeter and hematocrit detector and a method of use are disclosed. The tips of the optical fibers employed are beveled at an angle optimized to minimize internal reflections, allowing the use of the fibers to simultaneously perform transmitting and receiving functions.

5 Claims, 4 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

FIBER-OPTIC OXYGEN SATURATION/HEMATOCRIT SENSOR

BACKGROUND OF THE INVENTION

The present application relates generally to optical medical sensors, and in more particular relates to fiber-optic oxygen saturation sensors.

Traditionally, fiber-optic oxygen saturation sensors have taken the form of two or more optical fibers mounted parallel to one another within a catheter. Red and infrared light are applied to the proximal end of one of the fibers, and are emitted at the distal end of that fiber. The red and infrared light is reflected by the bloodstream, and enters the distal end of the second optical fiber. Light exiting the proximal end of the second fiber is measured in order to determine the relative intensities of reflected red and infrared light. Such a measuring system is included in U.S. Pat. No. 4,776,340, issued to Moran et al, included herein by reference in its entirety. While single optical fiber sensors are known for use in conjunction with measuring chemical parameters of the blood, such as $pCO_2$, $pO_2$ and pH, fiber-optic reflectance oximeters have typically employed two or more fibers.

Optical hematocrit detectors have traditionally employed two light sources and a single detector or two detectors and a single light source to provide two different source to detector spacings. As translated into a fiber-optic hematocrit sensor, this has resulted in the construction of hematocrit detectors employing three fibers. One such hematocrit detector is disclosed in the above cited Moran et al patent.

SUMMARY OF THE INVENTION

In the context of a reflectance oximeter, the inventors have determined that if the same fiber is used both to transmit and to receive, internal reflectance of the light transmitted down the fiber from the light source is typically of large enough magnitude to interfere with the ability to accurately measure the reflected light, entering the distal end of the optical fiber. This problem also arises in the context of a fiber-optic hematocrit detector, if one fiber is used to simultaneously perform transmitting and receiving functions. The present invention avoids the problem of internal reflectance to a degree sufficient to produce a workable two fiber hematocrit detector. This is accomplished by grinding the distal ends of the optical fibers at the same desired angle such that light reflected internally by the distal surfaces of the optical fibers will not propagate proximally up the fibers to a degree which interferes with measurement of light reflected from the bloodstream. While angling the ends of optical fibers, as is known in the context of fiber-optic connectors and combiners, it is believed that the inventors are the first to recognize that polishing the ends of the optical fibers at particular optimized angles allows the production of a two-fiber oxygen saturation and hematocrit detector.

DETAILED DESCRIPTION OF THE DRAWINGS

Figure 1:
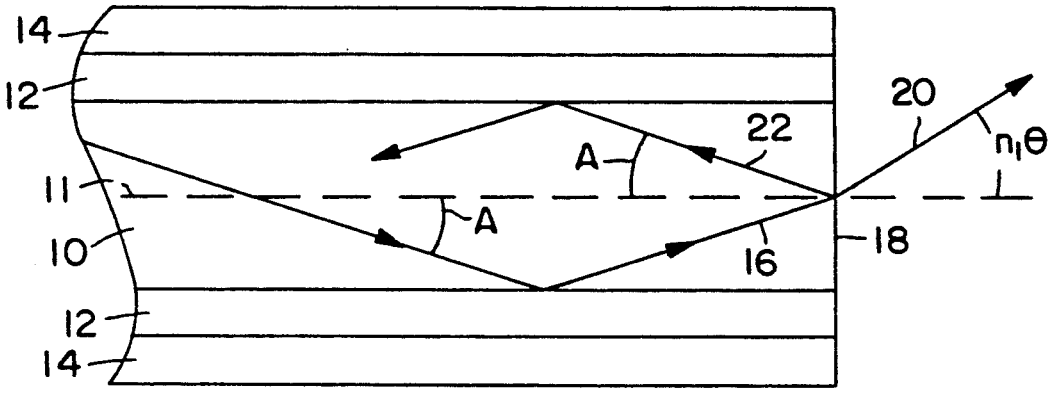
FIG. 1 PRIOR ART
FIG. 1 is a sectional view of the distal end of an optical fiber as typically used in prior art fiber-optic hematocrit detectors.

FIG. 1 shows a side, sectional view through the distal end of an optical fiber of the type typically used in conjunction with prior art reflectance oximeters. The particular fiber illustrated takes the form of a step index optical fiber in which the core 10 has a uniform refractive index, with a distinct change or step between the index of the core 10 and the cladding 12. The fiber is surrounded by a light absorptive jacket 14. The passage of a ray of light 16 down the optical fiber and out its distal end is illustrated. Propagation of light ray 16 down the optical fiber is accomplished by means of internal reflection at the boundary between the core 10 and the cladding 12. So long as the angle A of the ray of light 16 with respect to the axis 11 of the fiber is less than a maximum angle $\theta$, ray 16 will be completely reflected and will be propagated along the length of the optical fiber.

The maximum angle $\theta$ for total internal reflectance is defined by the refractory indices of the core and cladding of the fiber. One method of calculating this maximum angle is set forth in the book *Optical Fiber Telecommunications,* by Miller et al, Academic Press, 1979, so long as the angle defined by the ray, relative to the axis of the fiber, is less than or equal to $(2\Delta)^{\frac{1}{2}}$, total internal reflection will occur. In this case, $\Delta$ is the difference between the refractive indices of the core and the cladding of the fiber at their boundary.

While this is a somewhat simplified view of the propagation of light in an optical fiber, it will suffice for illustrative purposes in conjunction with the present invention. At the distal end 18 of the optical fiber, ray 16 is split into a refracted component 20 and a reflected component 22. Because the distal surface 18 of the fiber is perpendicular to the axis of the fiber, the reflected component 22 also intersects the cladding 12 at an angle A less than the maximum angle $\theta$ with respect to the axis 11, and will be propagated back up the optical fiber.

In addition to light reflected from the distal surface 18 of the fiber which defines an angle with respect to the fiber axis 11 less than the maximum angle $\theta$, rays defining an angle greater than $(2\Delta)^{\frac{1}{2}}$ but defining an actual angle of incidence with the boundary between the core and the cladding less than $(\pi/2)-(2\Delta)^{\frac{1}{2}}$ will be partially propagated back up the fiber. The angle of incidence is the angle defined between the ray and aligned perpendicular to the core/cladding boundary, intersecting the point of incidence of the ray with the core/cladding boundary. The degree of attenuation of these "leaky rays" depends upon the particular materials and construction used in the optical fiber. However, generally, the longer the fiber, the fewer of the "leaky rays" that will propagate along its entire length.

Propagation of the reflected component of ray 16 back up the optical fiber is not a problem in the traditional, two fiber reflectance oximeter. One fiber is used to transmit light, the other to receive. However, the inventors have determined that for optical fibers of lengths appropriate for use in catheters or other medical applications (typically less than two meters), light reflected internally off of the distal face of the optical fiber has a substantial amplitude as compared to the light entering the distal end of the fiber, reflected by the bloodstream. In an optical fiber having a perpendicular end surface, this can produce an undesirably high noise level.

Figure 2:
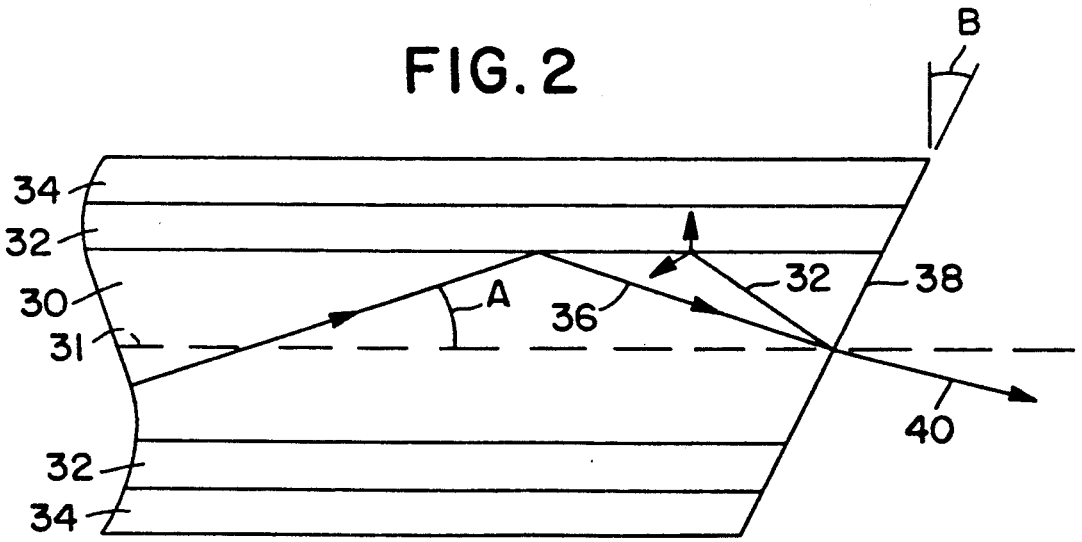
FIG. 2 is a sectional view through the distal end of an optical fiber adapted for use in the present invention.

FIG. 2 shows a side, sectional view through the distal end of an optical fiber appropriate for use in the present invention. The fiber is of the same sort illustrated in FIG. 1, having a core 30 with a uniform refractive index, with a step change between the index of the core 30 and the cladding 32. Similarly, the fiber is covered with an absorptive jacket 34. A ray of light 36 is illustrated as it moves down the fiber in a distal direction. The ray 36 defines an angle A with respect to axis 31, which is equal to the maximum angle $\theta$, and the ray 36 is thus completely reflected at the cladding 32. In the fiber of FIG. 2, the distal end 38 is beveled at an angle B with respect to the axis of the fiber. As in FIG. 1 above, ray 36 is divided into a refracted portion 40 and a reflected portion 42 at the distal end surface 38 of the fiber. However, because distal end 38 of the fiber is angled, the reflected portion 42 of the light ray will define an angle relative to the axis greater than the original ray 36. Making the angle B at which the fiber is beveled is greater than the maximum angle $\theta$ ensures that the angle which reflected ray 42 defines with respect to the axis will be greater than the maximum angle $\theta$. In this case, the reflected ray 42 will itself be divided into a refracted portion 44 and a reflected portion 46 of diminished amplitude by comparison to the original reflected portion 42.

By angling the distal end 38 of the fiber, internal reflectances can be reduced to a sufficiently low level so as not to interfere with measurement of light reflected by the blood, entering distal end 38 of the optical fiber. This allows for the construction of a practical two fiber hematocrit detector.

Figure 3:
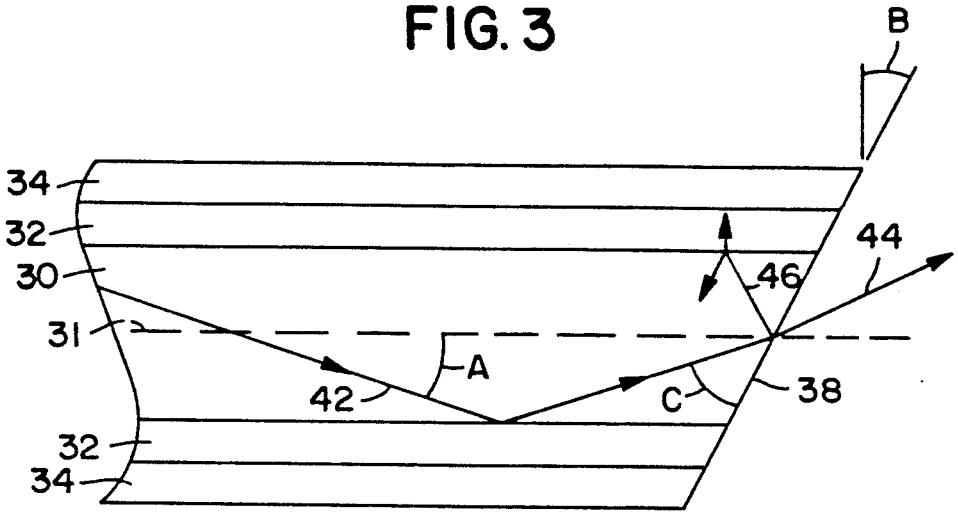
FIG. 3 is a second sectional view through the distal end of an optical fiber adopted for use in the present invention.

FIG. 3 illustrates the propagation of a ray 42 down the optical fiber illustrated in FIG. 3. Ray 42 defines an angle A with respect to the axis 31 which is equal to the maximum angle $\theta$ for complete internal reflection. Ray 42 intersects the distal surface 38 of the fiber at an angle C which is substantially reduced due to the angling of the end of the fiber. The angling of the distal end of the fiber still results in a reflected ray 46 which defines an angle with respect to the axis 31 greater than the maximum angle $\theta$.

Like the interface between the fiber core 30 and the cladding 32, the interface between the fiber core 30 and the environment exterior to the fiber defines a maximum angle for total reflection. As angle C approaches this maximum angle, the percentage of light escaping the distal end of the fiber decreases. In circumstances in which LED's or other limited output light sources are intended to be used, this may become an important consideration. Therefore, it is suggested that angle B should be beveled no more than necessary to bring internal reflections down to an acceptable level and in no case should the sum of angle B plus the maximum angle $\theta$ plus the equivalent maximum angle for the interface between the distal end 38 of the fiber and the surrounding exceed 90°. In catheters intended for use within human blood, either in which the distal end of the fiber is exposed directly to the blood, or surrounded by a plastic coating having a refractive index similar to blood, this results in an appropriate maximum angle B of not more than about 40° for most optical fiber types.

Selecting an appropriate angle B is complicated somewhat by the short lengths of the fibers involved. In medical applications, the lengths of optical fibers used may be short enough to allow for propagation of so called "leaky rays" (rays which are mostly reflected, but somewhat refracted) along the fiber from its distal end, back to its proximal end. This phenomenon is reduced both as the fiber length is increased and as the angle B is increased.

It appears that by setting the angle B roughly equal to the half angle of the acceptance cone of the fiber $(N_1(2\Delta)^{\frac{1}{2}})$ an appropriate accommodation of the various considerations involved can be reached. In this equation, $N_1$ equals the refractive index of the core, and $\Delta$ equals the difference between the refractive indices of the core and cladding.

While the optical fiber illustrated in FIGS. 2 and 3 is a step index fiber, the general approach set forth herein is equally applicable to graded index and other forms of optical fibers. With these fibers, as with step index fibers, the angle chosen should be the minimum angle necessary to reduce internal reflections to an insignificant point to preserve maximum efficiency of the fiber.

Figure 4:
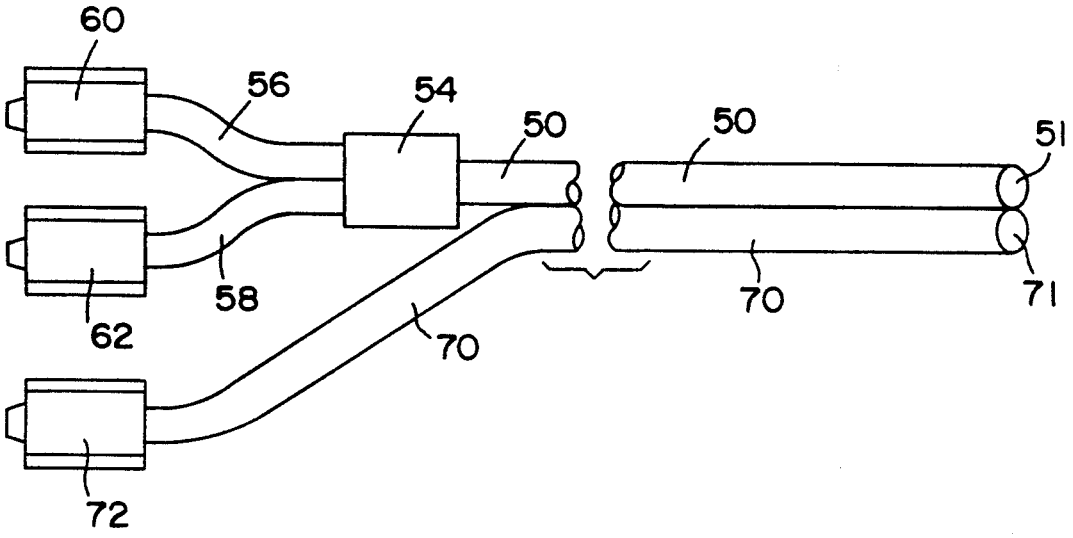
FIG. 4 is a bottom, plan view of a fiber-optic reflectance oximeter/hematocrit detector according to the present invention.

FIG. 4 shows a bottom, plan view of a two-fiber reflectance oximeter/hematocrit detector according to the present invention. The main body is comprised of optical fibers 50 and 70, which have their distal ends 51 and 71 ground at an angle, as discussed above.

Preferably, fibers 50 and 70 are attached to one another by suitable adhesive prior to grinding of their distal ends to the desired angle. This assures that light exiting one fiber will not directly enter the adjacent fiber, which would be possible if the ends were angled toward each other. It also maximizes the possibility that light emitted from one fiber will be reflected into the other fiber, which might be substantially reduced if the ends of the fibers were angled away from one another. This procedure also tends to equalize the light gathering abilities of the two fibers and also minimizes performance differences between individual sensors.

At its proximal end, fiber 50 is coupled to an optical splitter/combiner 54. Exiting the proximal end of splitter/combiner 54 are two optical fiber paths 56 and 58 which are provided with fiber-optic connectors 60 and 62, respectively. Connector 60 is intended to be coupled to a source of infrared and red light, and connector 62 is intended to be coupled to an optical receiver for measuring reflected light. In use, red and infrared light are transmitted distally down fiber 50, where they exit the distal end 52 of the fiber. The red and infrared light is reflected by blood cells adjacent the distal end 52 of the fiber, with the amount of red light reflected varying depending upon the degree to which the hemoglobin in the blood cells is saturated oxygen. Light reflected by the blood reenters the distal end 52 of the fiber and is propagated proximally on the fiber through splitter/combiner 54 to a detector for measuring amplitude of the reflected light. The ratio of reflected infrared to red light measured through connector 62 may be used to calculate oxygen saturation.

The proximal end of fiber 70 is provided with an optical connector 72. Connector 72 is adapted to be coupled to a second detector for measuring the amplitude of reflected light. The reflected red and infrared light as measured at optical connector 72 may also be used to calculate oxygen saturation. In this sense, fibers 50 and 70 would be used in the same fashion as traditional, two-fiber reflectance oximeter. In addition, the reflected infrared light measured at optical connector 62 and optical connector 72 may be used to calculate the hematocrit of the blood. In some embodiments, it may be desirable to located the detector in a multi-function catheter and/or to protect it from damage by means of a plastic casing as in the above cited Moran et al patent.

Figure 5:
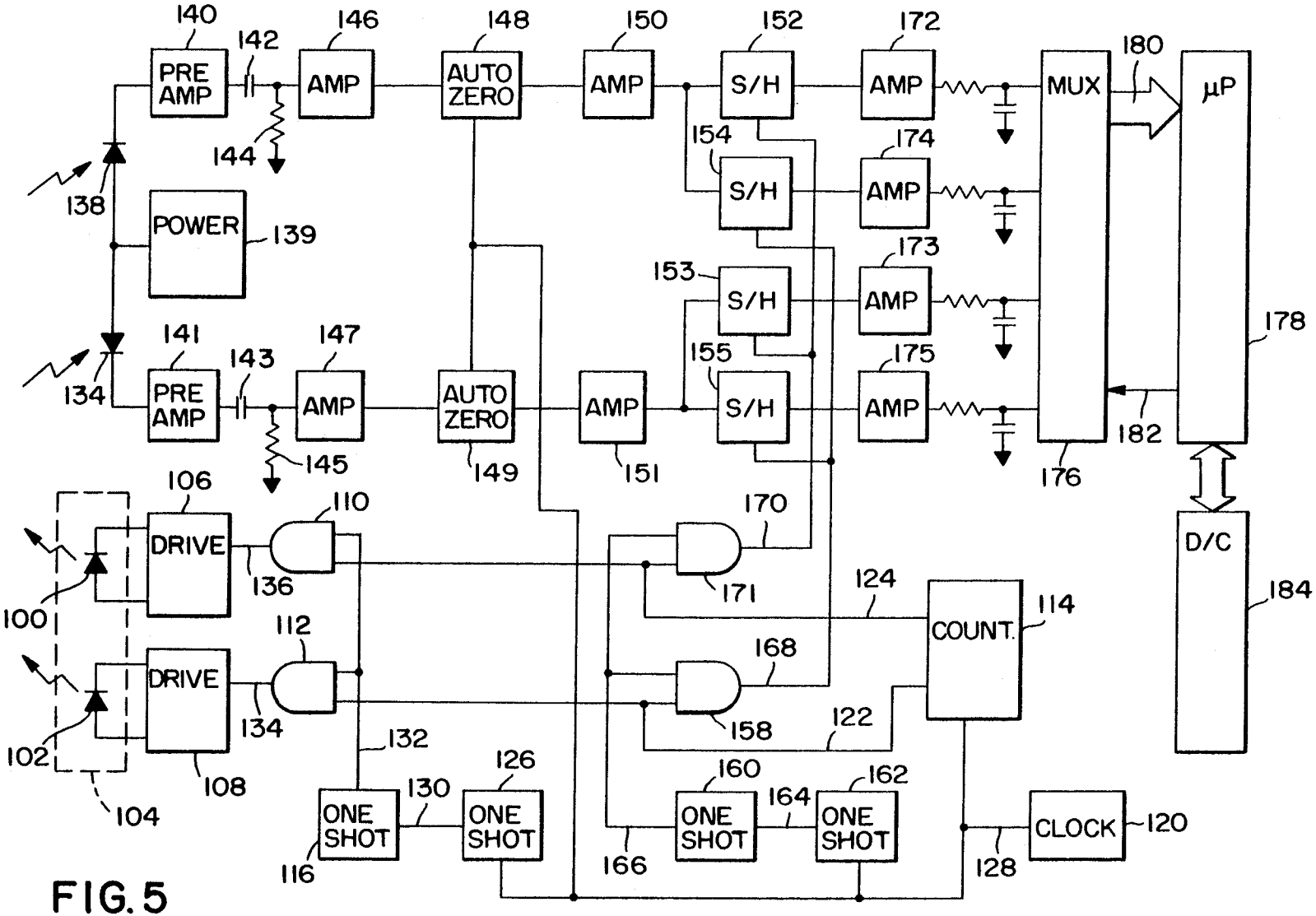
FIG. 5 is a functional block diagram of an apparatus for measuring oxygen saturation in conjunction with the fiber-optic oximeter of FIG. 4.
Figure 6:
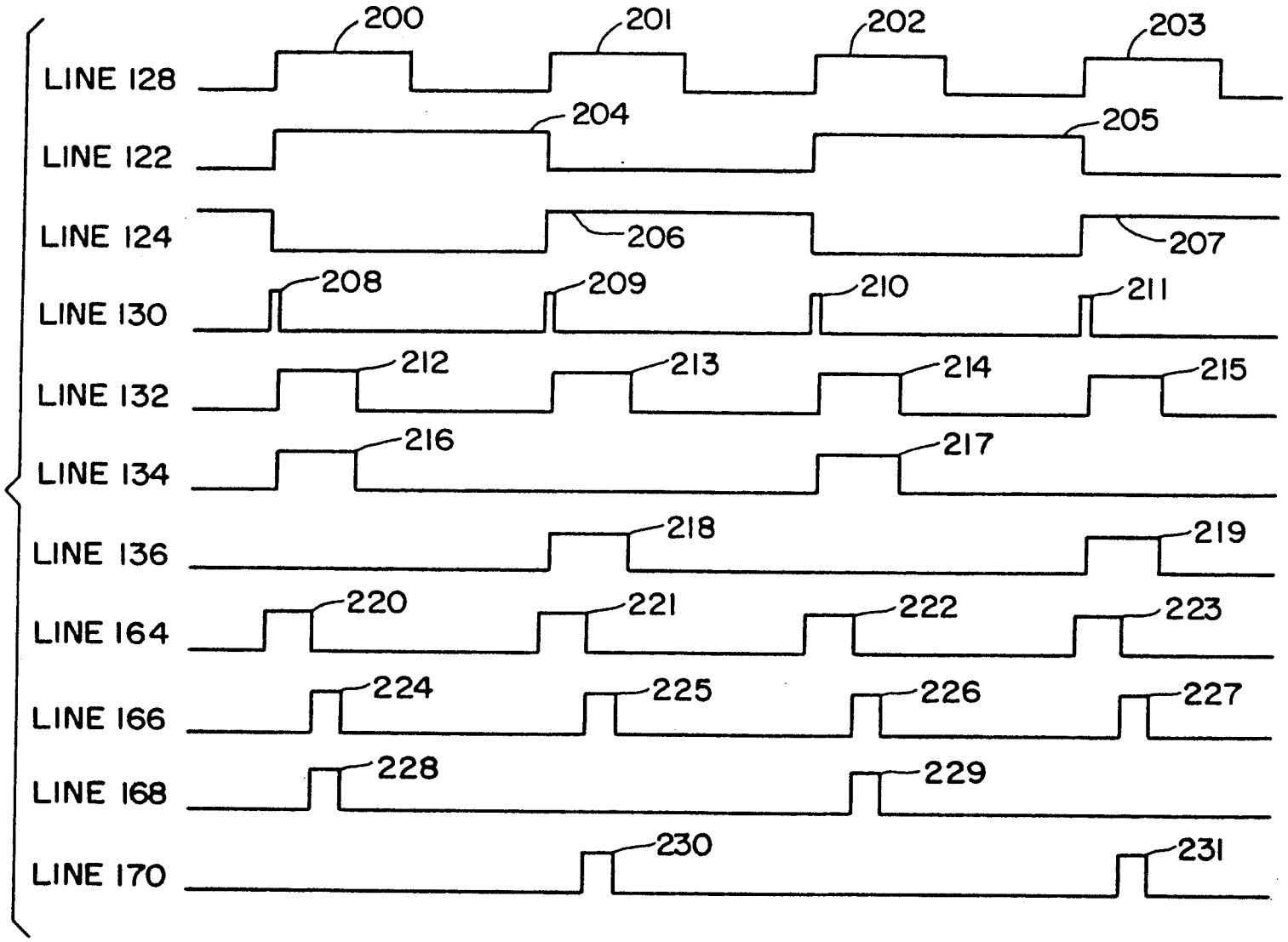
FIG. 6 is a timing diagram illustrating the operation of the apparatus of FIG. 5.

FIG. 5 is a functional, block diagram of an apparatus appropriate for use in conjunction with the sensor of FIG. 3 to measure oxygen saturation and hematocrit. LEDs 100 and 102 are red and infrared LEDs, respectively, may be mounted to a single substrate, indicated by dotted line 104, and positioned adjacent the end of a single optical fiber, as disclosed in U.S. Pat. No. 4,725,128, issued Nov. 20, 1985 to Bornzin et al, for a METHOD AND APPARATUS FOR DELIVERING LIGHT FROM MULTIPLE LIGHT EMITTING DIODES OVER A SINGLE OPTICAL FIBER, incorporated herein by reference in its entirety.

The operation of the components of this apparatus is best understood in conjunction with the timing diagram illustrated in FIG. 5. Clock 120 generates clock signals 200, 201, 202, 203 on line 218 which define a clock cycle time of 280 ms. Clock signals are applied to counter 114 which alternately generates 280 ms signals 204, 205 on line 122 which define the measurement cycles for the infrared LED 102 and corresponding signals 206, 207 on line 124 which define the measurement cycles for the red LED 100. With the beginning of each new clock cycle, delay one shot 126 is activated, generated 10 ms trigger signals 208, 209, 210, 211 on line 130. The trailing edges of these trigger signals start one-shot 116. One-shot 116 provides 80 ms signals 212, 213, 214, 215 on line 132 which define the on-times of the LEDs 100,102. For example, when signal 212 is present on line 132 and signal 204 is present on line 122, AND gate 112 generates a signal 216 on line 134 which activates the infrared LED 102 via LED driver 108. Similarly, when signal 213 is present on line 132 in conjunction with signal 206 on line 124, AND gate 110 generates a signal 218 on line 136, which activates red LED 100 via LED driver 106. Signals 217 and 219 on lines 134 and 136 are similarly generated. Thus, infrared LED 100 and red LED 102 are alternatively activated at spaced intervals from one another.

Measurement of the reflected light begins with the avalanche photodiodes 137 and 138, which are coupled to the fiberoptic catheter via optical couplings 62 and 72 (FIG. 4). Avalanche photodiodes 137 and 138 are powered by means of a −180 volt power supply 139. The signals from photodiodes 137 and 138 are applied to preamplifiers 140 and 141, and then passed through the filters comprising capacitors 142,143 and resistor 144,145 to amplifiers 146,147. The amplified signals pass through autozeroing circuits 148,149 to buffer amplifiers 150,151. Autozeroing circuits 148,149 are operated by clock pulses on line 128 to assure that the inputs to buffer amplifiers 150,151 are set to 0 between each measurement cycle. The output of buffer amplifiers 150,151 are provided to sample and hold circuits 152, 153, 154 and 155 which are alternately activated via logic gates 156 and 158.

With each clock cycle 200, 201, 202, 203 on line 128, delay one-shot 162 is activated, and produces 50 ms trigger pulses 220, 221, 222, 223 on line 164. It should be noted that trigger trailing edges pulses 220, 221, 222, 223 occur after the activation of the red and infrared LEDs 100 and 102. This is important because the trailing edges of the trigger pulses 220, 221, 222, 223 initiate the measurement of reflected light, which should be delayed until the output of the LED then activated has stabilized. Typically, a period of at least 30 microseconds is sufficient to accomplish this stabilization. Signals 220, 221, 222, 223 on line 164 trigger one-shot 160 to generate 30 ms sample and hold enabling signals 224, 225, 226, 227 on line 166. The sample and hold enabling signals, in conjunction with the signals, 205, 206, 207 on lines 122 and 124 serve to alternately activate sample and hold circuits 152 and 153 and sample and hold circuits 154 and 155. For example, when signal 204 on line 122 and signal 224 on line 166 are present, logic gate 158 produces an infrared sample signal 228 on line 168 which allows sample and hold circuits 152 and 153 to sample the outputs of buffer amplifiers 150 and 151. While signal 225 on line 166 is present along with signal 206 on line 124, logic gate 171 generates a red sample and hold enable signal 230 on line 170, which enables sample and hold circuits 154 and 155 to measure and store the output of buffer amplifiers 150 and 151. As noted above, between the activations of the sample and hold circuits, the clock signals on line 128 act to reset the autozeroing circuits 148 and 149 to zero the input signals to buffer amplifiers 150 and 151.

The outputs of sample and hold circuits 152, 153, 154 and 155, respectively, are amplified by amplifiers 172, 173, 174 and 175 and then provided to A/D multiplexer 176, which transforms them into digital data and presents them to microprocessor 178 via bus 180. Microprocessor 178 sequentially selects the outputs of amplifiers 172, 173, 174 and 175 for A/D conversion via select line 182. Microprocessor 178 may be any commercially available microprocessor. For purposes of experimental work, the inventors have found that an NEC brand lap top multispeed computer is satisfactory.

The measured reflected infrared and red light, entered in microprocessor 178 via bus 180 may be used to calculate the oxygen saturation and hematocrit of the blood according to stored look-up tables of actual measured values at known oxygen saturation and hematocrit levels and displayed on display 184, which may be CRT, LCD, paper chart recorder or other appropriate display apparatus.

Hematocrit corrected oxygen saturation values may similarly be calculated using either approach, based on a library of measurements of blood samples having known oxygen saturation and hematocrit. Once the hematocrit has been determined, it can be used to correct the oxygen saturation measurement, taken either using the ratio of infrared to red light reflected at connector 62 or at connector 72.

The measurement system set forth in FIG. 5 is intended to be exemplary, rather than limiting with regard to the type of measurement systems that are appropriate for use with a reflectance oximeter/hematocrit detector according to the present invention. Other similar measurement systems, such as that disclosed in U.S. Pat. No. 4,776,340 issued to Moran et al may also be appropriate. This patent is incorporated herein by reference in its entirety. An alternative measurement system which could be adapted for use with the oximeter of the present invention is disclosed in the thesis "Fiberoptic Probe For Intravascular Blood Gas Monitoring", submitted to the Faculty of the Graduate School of the University of Minnesota by Jeffrey Allan Schweitzer in November 1988. This thesis is also incorporated herein by reference in its entirety.

It is anticipated that in many cases the fiber-optic oximeter/hematocrit detector of the present invention will be incorporated in catheters capable of measuring a plurality of blood gas parameters, such as the catheter disclosed in U.S. patent application Ser. No. 07/314,615, for "BLOOD GAS MONITORING SENSORS", filed Feb. 23, 1989 by Schweitzer et al. This patent application is also incorporated herein by reference in its entirety.

In conjunction with the above specification, we claim:

1. A reflectance oximeter/hematocrit detector, comprising:

first and second optical fibers, each of said optical fibers having a proximal end and a distal end, the distal ends of said optical fibers each being beveled to define an acute angle with respect to a line perpendicular to the axis of said fibers;

means for generation of red and infrared light;

means for measuring red and infrared light;

first optical coupling means for coupling said means for generating red and infrared light to the proximal end of at least one of said two optical fibers; and second optical coupling means for coupling said means for measuring light to the proximal ends of both of said at least two optical fibers.

2. An apparatus according to claim 1 wherein said means for generating red and infrared light comprises means for sequentially generating red and infrared light.

3. An apparatus according to claim 2 wherein said means for measuring light comprises means for sequentially measuring red and infrared light emitted from the proximal ends of both of said two optical fibers.

4. An apparatus according to claim 1 or claim 2 or claim 3 wherein said acute angle defined by the beveled distal ends of said optical fibers is approximately equal to the half angle of the cone of acceptance of said at least two optical fibers.

5. An apparatus according to claim 1 or claim 2 or claim 3 wherein said distal ends of said optical fibers are coplanar.

* * * * *